United States Patent
Morozov et al.

(10) Patent No.: US 8,597,932 B2
(45) Date of Patent: *Dec. 3, 2013

(54) CELL CULTURE OF MICORRHIZAL FUNGUS AND ARTHROBACTER HISTIDINOLOVORANS

(75) Inventors: Victor Morozov, Manassas, VA (US); Charles L. Bailey, Cross Junction, VA (US); Nikolai N. Vsevolodov, Kensington, MD (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 1984 days.

This patent is subject to a terminal disclaimer.

(21) Appl. No.: 11/419,593

(22) Filed: May 22, 2006

(65) Prior Publication Data

US 2006/0273187 A1    Dec. 7, 2006

Related U.S. Application Data

(60) Provisional application No. 60/682,831, filed on May 20, 2005.

(51) Int. Cl.
*C12P 1/02*     (2006.01)
*A61K 9/14*     (2006.01)

(52) U.S. Cl.
USPC .......... 435/254.1; 435/41; 435/171; 435/243; 424/400; 424/489; 424/493; 424/93.5

(58) Field of Classification Search
USPC .......... 424/400, 489, 493, 93.1, 93.5; 435/41, 435/171, 243, 254.1
See application file for complete search history.

(56) References Cited

U.S. PATENT DOCUMENTS

| 4,401,755 | A * | 8/1983 | Weaver | 435/34 |
| 6,114,153 | A * | 9/2000 | Shukla et al. | 435/91.2 |
| 2002/0022265 | A1 * | 2/2002 | Bailey et al. | 435/325 |

* cited by examiner

*Primary Examiner* — Ruth Davis
(74) *Attorney, Agent, or Firm* — David Yee; David Grossman; Edgar Rodriguez (57) ABSTRACT

The invention involves developing and stabilizing cultivating droplets within a matrix of a porous medium. A cultivation medium may be selected, prepared and mixed with a surfactant. Where cells are desired to be cultured in droplets, cells may be added. The mixture may be converted into cultivating droplets. The cultivating droplets may be stabilized by introducing them to a porous medium. The porous medium may contain hydrophobic particles. Stabilized, cultivating droplets having one or more cells may form an aseptic microenvironment for the concentrated growth of cells.

16 Claims, 9 Drawing Sheets

CELL CULTURE OF MICORRHIZAL FUNGUS AND ARTHROBACTER HISTIDINOLOVORANS

CROSS REFERENCE TO RELATED APPLICATIONS

The present application claims the benefit of provisional patent application Ser. No. 60/682,831 to Morozov et al., filed on May 20, 2005, entitled "Cell Culture," which is hereby incorporated by reference.

DETAILED DESCRIPTION OF THE INVENTION

The invention involves suspending cultivatable droplets in a porous medium, where each droplet includes a mixture of a cultivation medium and a surface-active agent or compound. Both surface-active agent and surface-active compound may be hereinafter referred to as surfactant. Each droplet may provide an encapsulated microenvironment for the addition of a plurality of cells to be cultured with minimal to no contamination. The droplets may be transported while the cells are being cultured.

Culturing microbial, animal or plant cells are crucial processes that are essential to the production of a wide array of useful chemical and biochemical products. Living cells are employed in such processes because they may provide essential elements necessary to economically synthesize many commercially valuable metabolic products.

Typically, growing cells are cultured either on the surface of a solid nutrient (surface cultivation) or in cultivation media (submerged cultivation). Microorganisms, such as bacteria and fungi, can be cultured using either the surface or submerged method. Eukaryotic cells can be cultured in a submerged or suspended cell culture in rolling flasks. Alternatively, where cell surface attachment is necessary, eukaryotic cells can be grown in confluence in tissue culture flasks with a cultivation nutrient media. A suitable nutrient medium for microorganisms often includes a carbon and energy source, an assimilable nitrogen source, oxygen (usually derived from surrounding air), and suitable pH conditions, as well as additional factors which vary for a given microorganism, as one skilled in the art can readily appreciate.

With the surface method, nutrients may be absorbed from contact with the media under the culture. Oxygen may be provided through contact with the air above the culture. Inhibitory metabolites may seep down and away from the culture. Surface cultivation of microorganisms has the advantageous features of providing a plentiful oxygen source from the surrounding air and efficient removal of inhibitory metabolites through absorption from the surface medium. Also, contamination of surface culture can be relatively confined to a minimal surface area or a growing culture.

However, surface cultivation of microorganisms tends not to be amenable to large scale production. The process of filling and inoculating numerous individual plates or dishes with culture, and then individually harvesting each plate, can be extremely labor intensive. Furthermore, the storage of solid surface plates or dishes inoculated with microorganisms requires significant allocations of space in sophisticated incubators.

With the submerged method, a microorganism may be cultured throughout the cultivation media. Nutrients may be absorbed from contact with the media surrounding the individual microorganisms. Oxygen may be provided by various means of aeration that one skilled in the art can readily appreciate. Metabolites may seep out and into the media. Usually, the nutrient media is also stirred continually to evenly distribute the microorganisms.

The submerged cultivation process has the beneficial advantages of being less labor and space intensive than the surface method. Such method can be used to produce large batches of cells in a relatively small space. Thus, the submerged method is usually the method of choice currently employed in most pilot and industrial scale production of cultured microorganisms and cells.

However, the submerged cultivation method may require an extensive investment in equipment necessary for the large scale production of cell cultures. In addition, the end products that are the object of large scale submerged cultivation (i.e., the intracellular or extracellular metabolic products of cell and microbe growth) usually require further purification and concentration either from the cultivation media or the cells therein. This additional isolation step is often necessary because the concentration of product in the media tends to be limited by the metabolites released into the media and by the solubility of oxygen and/or other gases in the media.

Another major drawback to the large scale submerged cultivation method is the greater risk and effects of contamination that this method entails. In submerged cultivation, the complexity of the equipment necessary for bacterial fermentation systems, for example, may provide more opportunities for contamination when compared to the surface growth methodology. Furthermore, once a culture is contaminated, the contamination can quickly spread throughout the agitated cultivation media, resulting in the destruction of the entire batch of a culture.

U.S. Pat. No. 6,649,408 can help resolve some issues. The '408 patent teaches culturing cells in microdroplet form. However, a major drawback involves retention of cells to be cultured in a specific microdroplet form and size. If retention cannot be achieved, cells may not be efficiently grown using the beneficial features of the submerged and surface cultivation, or grown in a stabile environment.

Figure 1:
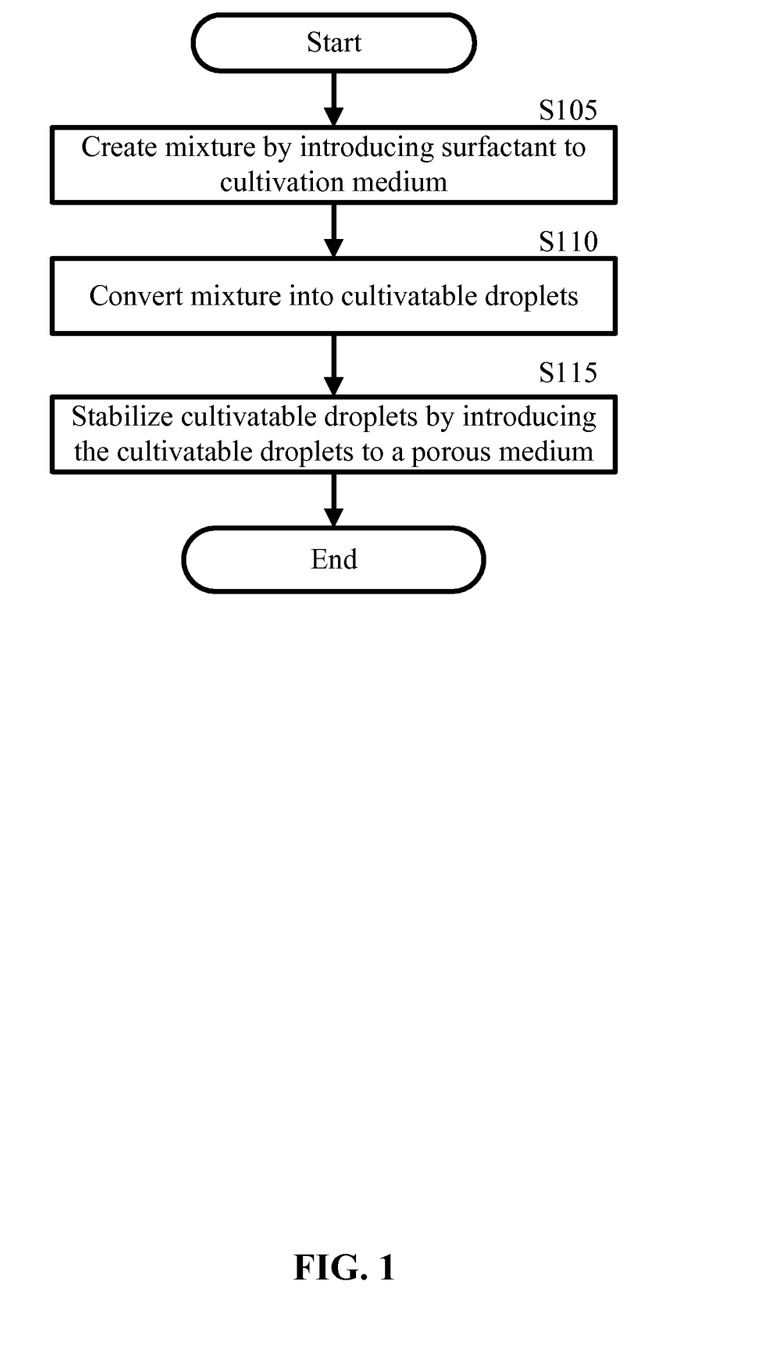
FIG. 1 shows a flow diagram of cell culturing, as per one aspect of the invention.

To retain and culture cells in an encapsulated form that is not limited to size, reference is now made to the drawings. FIG. 1 shows a general, embodied method of cultivating droplets. At least one surfactant may be introduced to a cultivation medium S105. This combination may create a mixture. The mixture may be converted into cultivatable droplets S10. The cultivatable droplets can be stabilized by introducing them to a porous medium S115.

Figure 2:
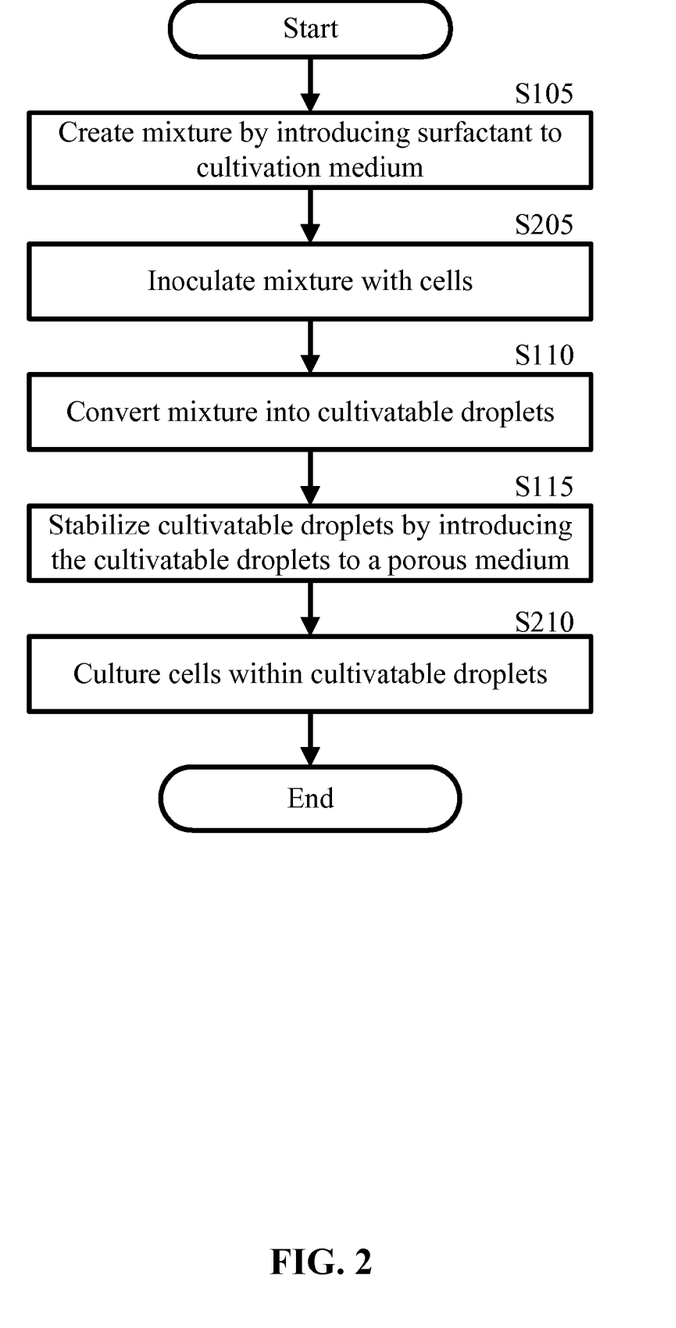
FIG. 2 shows another flow diagram of cell culturing, as per one aspect of the invention.

FIG. 2 shows another general, embodied method of cultivating droplets. Here, a plurality of cells may be introduced to the mixture prior to the mixture's conversion into cultivatable droplets S205. This combined mixture, which may be referred to as an inoculated mixture, may be converted into cultivatable droplets S110. These cultivatable droplets may be stabilized by introducing them to a porous medium S115. Each cultivatable droplet that contains one or more cell(s) may be grown and cultured S210.

It is also within the scope of the invention that the inoculated mixture be first introduced to hydrophobic particles prior to being converted into cultivatable droplets. These hydrophobic particles may be either different or the same as that of the porous medium.

The cultivation medium may be selected from a manufacturer and/or prepared according to the manufacturer's specifications. In selecting and/or preparing the cultivation medium, selection may depend on the cell intended for culturing. It should be noted that it is not necessary that the medium be in a liquid state. It is possible that the medium be in a semi-liquid, gel (e.g., 1% agar) or solid state. The cultivation medium may include electrolytes, sugars and/or other nutrients to serve as an energy source for cellular metabolism. For example, if *Pseudomonas aeruginosa*, an oil-eating bacteria, or *Pseudomonas putida*, a styrene-eating bacteria, were to be grown and nurtured, Nutrient Agar (BD 213000) or Nutrient Broth (BD 234000) may be used as the cultivation medium. For a guideline in choosing and/or preparing appropriate cultivation media, the American Type Culture Collection (ATCC) of Manassas, Va. may be consulted.

As one embodiment of the invention, a surfactant may be added to the cultivation medium during or after the cultivation medium's preparation. According to the International Union of Pure and Applied Chemistry (IUPAC) Compendium of Chemical Terminology, 2d ed. 1997, a surfactant is "a substance which lowers the surface tension of the medium in which it is dissolved, and/or the interfacial tension with other phases, and accordingly, is positively adsorbed at the liquid/vapour and/or at the interfaces".

The addition of surfactants tends to aid and facilitate the binding process between the cultivation media and hydrophobic particles. Surfactants include, but are not limited to, proteins, lipids, phospholipids, dextrans, collagen, gelatin, other natural and synthetic polymers, and derivatives thereof that would enable the cultivation medium to stick to hydrophobic surfaces. In one exemplified embodiment, proteins are added to the cultivation medium. Proteins tend to be irreversibly unfolded upon adsorption at the water interface. This characteristic may expose their polar groups to water and their nonpolar groups to air or a hydrophobic surface. Hence, if hydrophobic particles are introduced, these hydrophobic particles would likely bind with the exposed nonpolar groups.

However, it is also within the scope of the invention that a cultivation medium may have the capability of sticking to hydrophobic surfaces without the addition of a surfactant. In addition, a surfactant may not be necessary if the desired cells produce or have the capability to produce biological surfactants (biosurfactants) as well. In such cases, the cultivation medium may be inoculated with desired cells without having to include a surfactant. By lowering surface tension, biosurfactants can aid the cultivation medium in binding to hydrophobic surfaces. Nonlimiting examples of such cells include *Bacillus mojavensis, Bacillus subtilis, Bacillus licheniformis*, and *Bacillus sonorensis*. Each of these examples may be considered as good candidates for microbial oil recovery.

The mixture of surfactant and cultivation medium may be inoculated with a plurality of cells. Cells are defined to be either prokaryotic or eukaryotic. In essence, the cells may include, but are not limited to, microbial cells, fungal cells, bacterial cells, spores, T-cells, etc. Notably, it is also within the scope of the invention that cells that produce important chemical and biochemical products without any genetic alteration can be grown. Additionally, it is also within the scope of this invention that viruses, bacteriophages and other microscopic parasites be included in the plurality of cells. Moreover, the cells may be additionally infected with a microorganism (e.g., a virus, bacteria, bacteriophage, spore, fungus, etc.); transformed with a heterologous DNA and/or RNA expression vector; or otherwise genetically engineered to produce a given substance with techniques that are well known within the art.

Either mixture or inoculated mixture may be atomized into cultivatable droplets. Characteristically, each cultivatable droplet may appear slurry-like and have a semi-liquid consistency. In one embodiment, as illustrated in FIG. 3, each droplet may contain zero, one or more cells, as well as the cultivated medium with the addition of a surfactant. In another embodiment, cultivatable droplets may contain zero, one or more cells, as well as the cultivated medium without the addition of a surfactant.

As another embodiment, it is particularly recommended that the droplets be stabilized to achieve retention of mixture (with or without a surfactant, and with or without at least one cell) in droplet form. Stabilization can be accomplished by introducing the cultivatable droplets to a porous medium.

The porous medium may include hydrophobic particles (sometimes be referred to as hydrophobic beads or beads). In an embodiment, the porous medium is a hydrophobic powder. Hydrophobic particles may help protect the inoculated mixture from contamination, as well as water penetration from neighboring cultivatable droplets. An example of hydrophobic particles includes silanized silicon dioxide. However, it should be obvious to one skilled in the art that other hydrophobic particles (such as carbon sooth, aluminum oxide and zinc oxide) may be used.

In yet another embodiment, as illustrated in FIG. 4, fibrous powder containing fibers (e.g., hydrophobic microfibers, nanofibers, etc.) 405 may be used to stabilize the cultivatable droplets 410. These fibers may be hydrophobic. It is likely that suspending cultivatable droplets on a web of hydrophobic fibers may provide better stabilization since cultivatable droplets are not likely to be able to move as easily as they would when stabilized with nearly spherical nanoparticles.

Fiber suspension may also provide enhanced diffusion of oxygen and other gases through the system. Because fibers tend to be rigid, most of the space volume in fiber suspension is likely to be occupied by gas. The presence of gas provides a clear contrast to that of cultivatable droplet stabilization with spherical beads, which tend to densely populate space between liquid droplets. To create this fiber suspension, fibrous microcrystalline cellulose may be used. Such material may be chemically treated to make the surface of the microcrystals hydrophobic. Many hydrophobic polymers (e.g., polystyrene, polyethylene, etc.) may be extruded in the form of microfibers. Powder prepared from these fibers may be used to suspend the cultivatable droplets. To further increase efficiency of mixing cultivatable droplets coated with fibers, both cultivatable droplets and fibers may be oppositely charged.

In yet another embodiment, spherical hydrophobic particles may be mixed with fibrous particles to improve the stability of the system by introducing a fibrous component.

The fibrous component may serve as a carcass or a skeleton to support cultivatable droplets stabilized with spherical hydrophobic particles.

Additionally, hydrophobic particles need not be in powder form. The choice of hydrophobic particles will likely vary depending on the organism to be cultured and the amount of aeration required. Where silicon dioxide particles are used, such particles ought to be hydrophobic and ought to have a surface area between approximately 50 and 380 meters$^2$ per gram of weight.

One particular example of hydrophobic particles is the series of silanized Aerosil particles produced by DeGussa AG of Dusseldorf, Germany. These include, but are not limited to, Aerosil® R 104, Aerosil® R 106, Aerosil® R 202, Aerosil® R 805, Aerosil® R 812, Aerosil® R 812.S, Aerosil® R 972, Aerosil® R 974 and Aerosil® R 8200. By themselves, Aerosil particles are generally hydrophilic (like sand). However, Aerosil particles can become water repellent, and hence suitable for stabilizing cultivatable droplets, after being treated via silanization. Alternatively, similar natural materials may be used to achieve stabilization. Examples of similar natural minerals include, but are not limited to, carbon sooth (e.g., those obtained from diesel engines), ZnO powder and any inert solid hydrophobic material subjected to deep milling (e.g., elemental sulfur).

It is contemplated that the present composition of cultivatable droplets coated with hydrophobic particles will vary, depending on a multitude of factors. Factors include, but are not limited to, the cell type, the size of the individual droplets, and the desired final density and growth phase. In one embodiment of the invention, the ratio of individual hydrophobic particles to droplets may be within a range of 99:1 and 1:99. In another embodiment of the invention, the ratio of individual hydrophobic particles to inoculated mixture may be within a range of 2:1 and 1:2.

Generally, hydrophobic particles are held on the surface of water with weak Van der Waal's forces. It is well known in the art that the interface between a hydrophobic particle and water surface can be substantially stabilized in the presence of surfactants in a solution. This interaction is comparable to the well known phenomenon of soap bubbles. Apart from soap and other detergents, many other particles (e.g., activated carbon, activated alumina, etc.) are well known for their ability to adsorb liquids or gases. With respect to the invention, it is expected that the surfactant would anchor a hydrophobic particle at the cultivatable droplet surface once the surfactant adsorbs the hydrophobic particle.

Several factors and conditions may at times affect cultivatable droplet stabilization inside the matrix formed by hydrophobic particles and a cultivatable droplet. For example, one factor determining a cultivatable droplet's stability is the rheology of the cultivatable droplet size and aerosil media. Cultivatable droplet stabilization may be affected when the cultivatable droplet volume to aerosil volume ratio is relatively low. When this scenario occurs, cultivatable droplets on average tend to be positioned at great distances from each other. Until the cultivatable droplets become heavy enough to overcome weak forces (i.e., Van der Waal's forces) that keep aerosil particles together, these forces will probably prevent water droplets from sinking into the aerosil layer. It should be noted that droplets with a diameter exceeding approximately 3 mm typically sink to the bottom of the aerosil layer.

Furthermore, adding a fibrous component is expected to increase stability of the system by increasing critical sheer stress while moving through the porous medium. By overcoming the sheer stress level, larger cultivatable droplets can be suspended in the porous medium.

Figure 3:
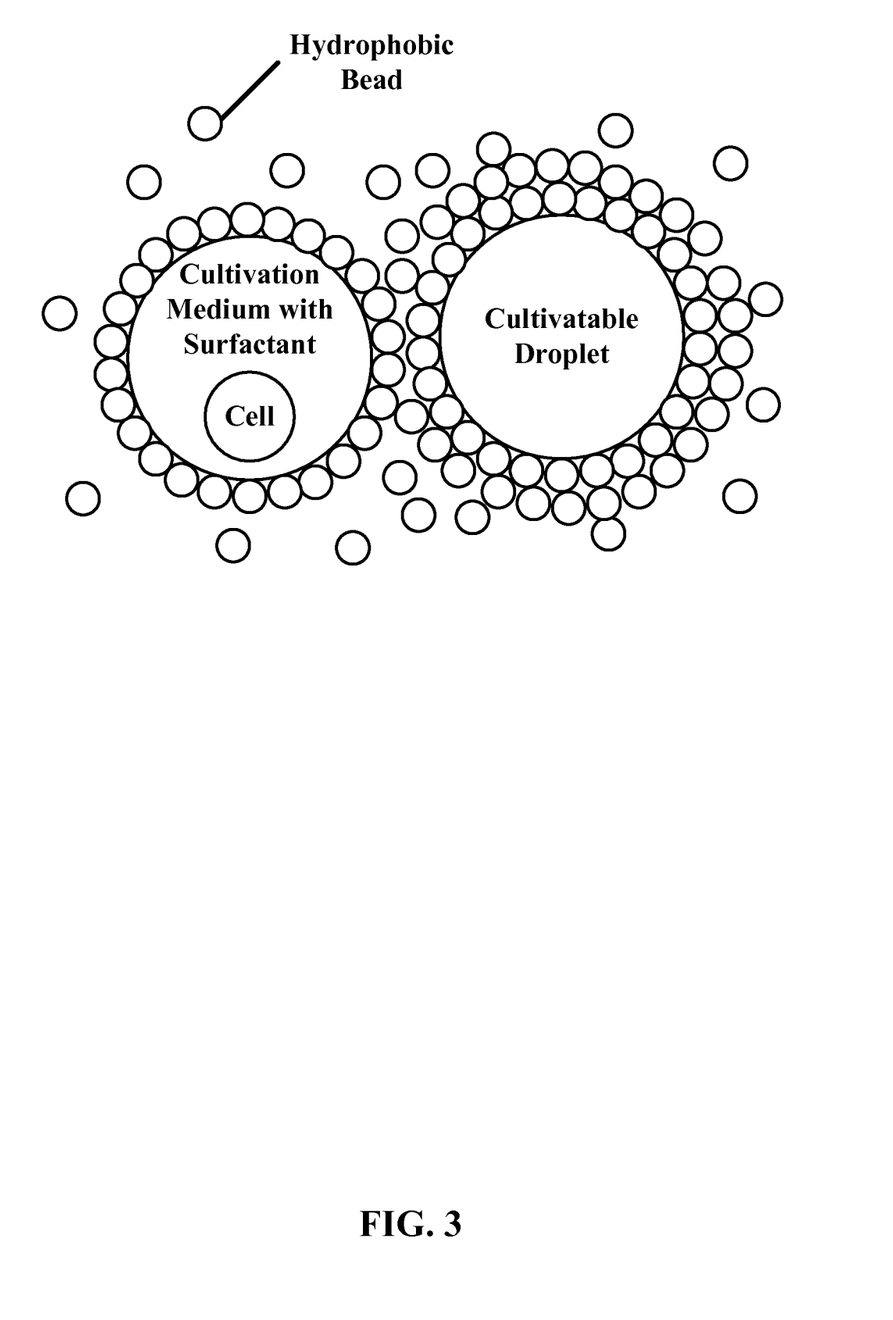
FIG. 3 shows stabilization of cultivatable droplets using hydrophobic beads from a hydrophobic powder.
Figure 4:
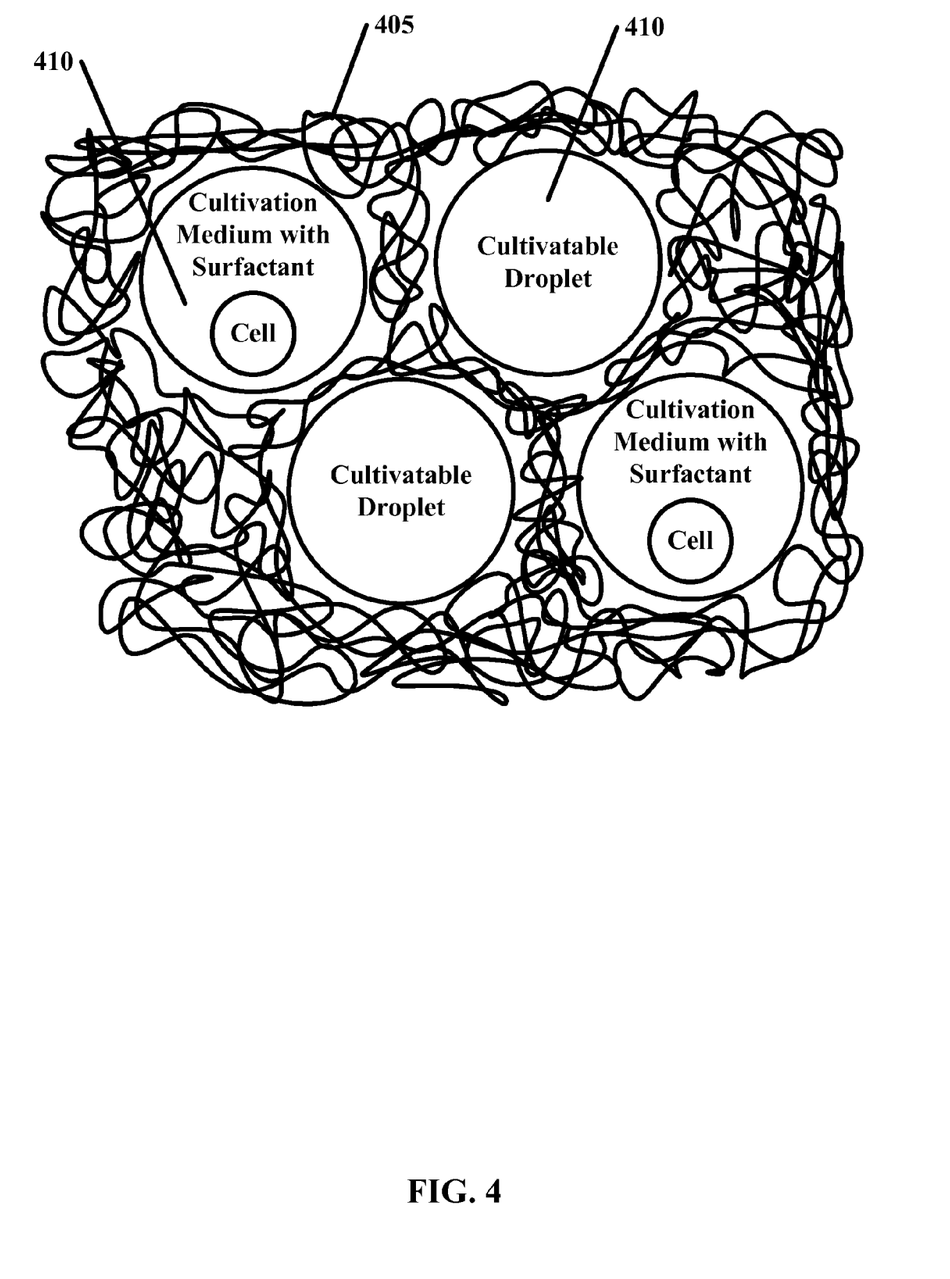
FIG. 4 shows stabilization of cultivatable droplets using hydrophobic fibers.

Cultivatable droplet stabilization may also be affected when the cultivatable droplet volume to aerosil volume ratio is relatively high. When this case occurs, cultivatable droplets may tend to come into contact with each other. Upon contact, cultivatable droplets may form a multilayer of beads between the surfaces of the cultivatable droplets, as shown in FIG. 3. Stability of such contacting cultivatable droplets may depend on how strongly beads are anchored to the cultivatable droplet surface. If the beads can be easily moved and/or displaced form the contact area, the cultivatable droplets may coalesce. However, if the beads are anchored and/or cannot easily move out of the water surface, cultivatable droplets may be stabile.

Figure 5:
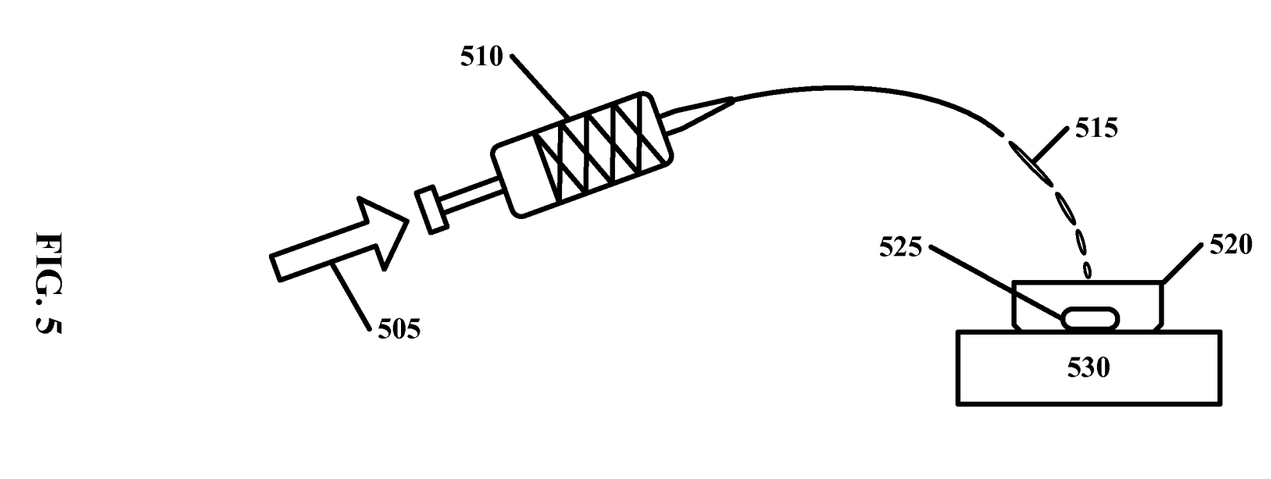
FIG. 5 shows a jetting technique, as per one aspect of the invention.

Various techniques may be used to create and stabilize cultivatable droplets. As an exemplified embodiment, inoculated mixture may be transformed into cultivatable droplets via a jetting technique. As shown in FIG. 5, cultivatable droplets 515 may be ejected from a thin capillary tip when pressure 505 is applied to a micro-syringe pump 510. To catch the cultivatable droplets 515, a container 520 lined with a porous medium (such as an aerosil layer) may be used. The porous medium can be a hydrophobic powder, fibrous powder, etc. The container 520 can be, but is not limited to, a Petri dish, beaker, cup, etc., to achieve a near uniform-to-uniform coating. The aerosil layer may be subjected to slow mixing using a bar magnet 525 and a magnetic stirrer 530, which can aid in controlling mixing speed. Hydrophobic fumed silica, such as Aerosil® R 972, having an average diameter of 16 nm, may be used. By varying the pressure and diameter of the tip, the size of a cultivatable droplet's diameter may be controlled. For example, a flow rate of about 8 mL/hour through a glass capillary tip ranging from about 30-50 μm can produce highly homogenous cultivatable droplets with average diameters between approximately 100-200 μm.

Figure 6:
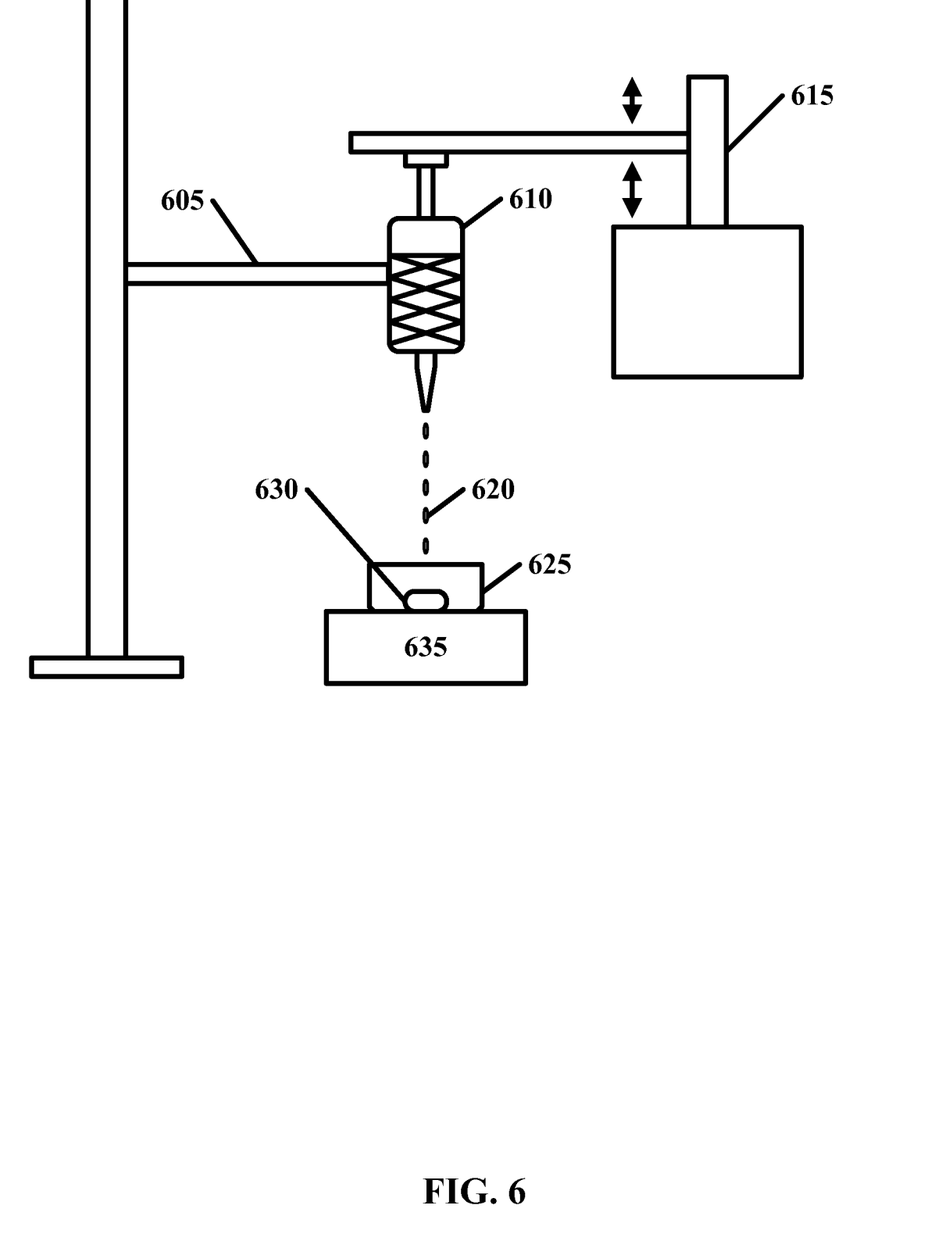
FIG. 6 shows yet another jetting technique, as per one aspect of the invention.

In one embodiment, as shown in FIG. 6, a system exercising the jetting technique may be created to automatically eject inoculated mixture from a micro-syringe 610 at a constant or variable rate (e.g., ~8±2 mL/hour, etc.). For instance, the micro-syringe 610 may be clamped 605, and the micro-syringe's pump may be pushed by a controlled mechanical device 615 with adjustable rate settings. A container 625 having an aerosil layer may be used to receive the cultivatable droplets 620. The system may also include a magnetic bar 630 and magnetic stirrer 635 to mix the cultivatable droplets with a porous medium (e.g., an aerosil layer). The porous medium can be a hydrophobic powder, fibrous powder, etc. Alternatively, pressure on the pump may be applied manually, similar to that as seen in FIG. 5. In another embodiment, a system containing inoculated mixture may be suspended to allow the inoculated mixture to drip into the container with hydrophobic fumed silica at a constant or variable rate (e.g., ~8±2 mL/hour, etc.). For example, solution may be placed in a bag, such as an IV bag, capable of being suspended. An aperture at one end of the bag may have a control valve to release inoculated mixture at a desired rate. In yet another example, a system using a pipette with a thin capillary tube and a control drip valve may be used to drip inoculated mixture at a constant (or even variable) rate (e.g., ~8±2 mL/hour, etc.) into the hydrophobic fumed silica. The pipette may be clamped vertically. By adjusting the pipette's control drip value, inoculated mixture may be released and controlled at a desired rate. Such rate may be predetermined with respect to time, amount (e.g., volume), etc.

Figure 7:
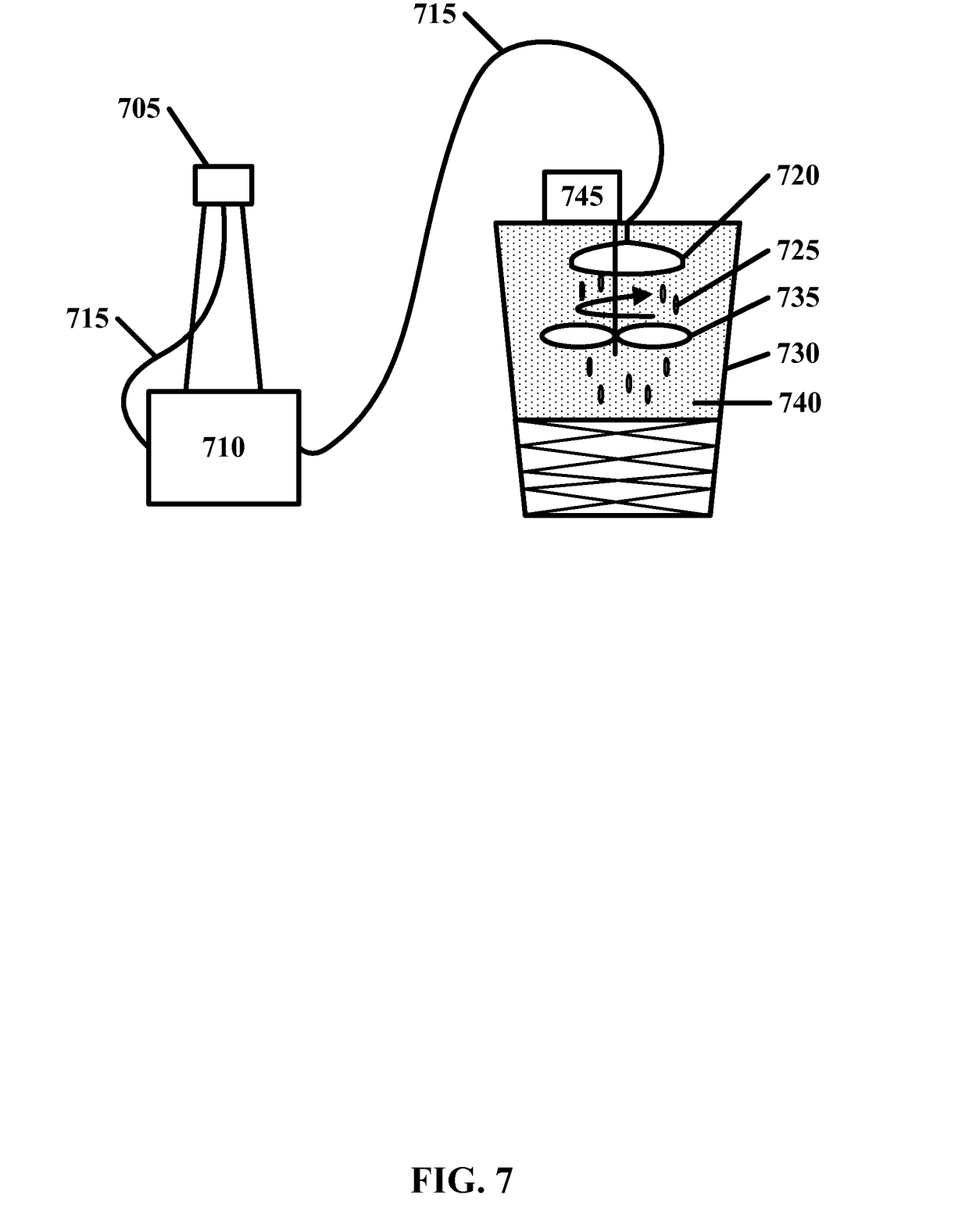
FIG. 7 shows a showering technique, as per one aspect of the invention.

Another technique is the showering technique. As shown in FIG. 7, an inoculator 705 having inoculated mixture may be connected to a pump 710. Using nozzles 715, the pump (which may include a motor) may pump inoculated mixture from the inoculator 705 to a sprayer 720. Droplets may be formed by using the sprayer 720 having an array of holes to disperse inoculated mixture. The sprayer 720, which can resemble a shower head, may be created by punching holes in a Teflon film. Holes may vary in diameter, for example, from 50-100 μm. Alternatively, a shower head may be used. To catch cultivatable droplets 725, a vessel 730 (such as a bucket, can, jar, dish, beaker, etc.) may be used. The vessel 730 may include a porous medium (e.g., a cloud or layer of aerosil 740). The porous medium can be a hydrophobic powder, fibrous powder, etc. The presence of the cloud of aerosil 740 may enable effective coverage of dispersed droplets by aerosil particles. Because droplets 725 tend to be heavier than the aerosil particles 740, the droplets are likely to encounter the aerosil particles 740 and may be stabilized. As the inoculated mixture is sprayed into the vessel 730, the cultivatable droplets 725 formed may encounter a propeller 735 attached to a motor 745 before, at the same time or after encountering aerosil particles 740. Although not necessary, a propeller 735 may be used for distributing the cultivatable droplets 725 uniformly and/or stir the aerosil particles in a way such that cultivatable droplets 725 and aerosil particles 740 may make contact with each other. In other words, the spinning rate of the propeller 735 may be controlled with the motor 745 by the user.

Figure 8:
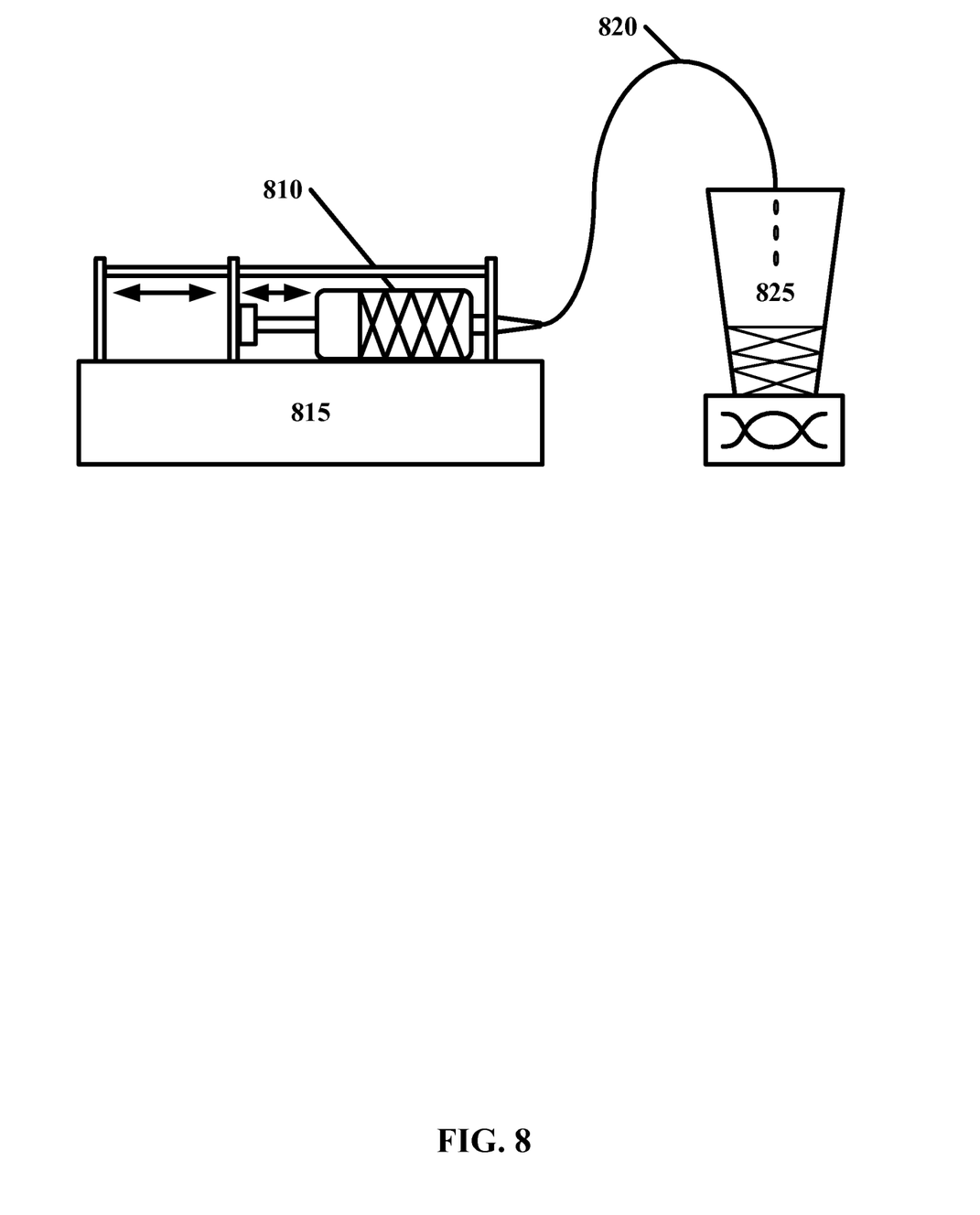
FIG. 8 shows a blending technique, as per one aspect of the invention.

Alternatively, the invention also allows for a third technique where inoculated mixture may be introduced to hydrophobic particles prior to conversion into droplet form. This technique is known as blending. Here, as shown in FIG. 8, using a pump 815 and nozzle 820, inoculated mixture may be pumped into a blender 825 having aerosil. It is possible that the pump 815 may pump inoculated mixture from a syringe 810 or some other form of container (such as a glass, jar, beaker, tube, etc.). Alternatively, inoculated mixture may be manually placed at the bottom of a blender 825 and overlayed with a porous medium (e.g., aerosil). The porous medium can be a hydrophobic powder, fibrous powder, etc. As an embodiment, the ratio of inoculated mixture to aerosil is about 1 to 4 (volume to volume). A cocktail of dispersed cultivatable droplets may be rapidly formed with the blender's knives revolving at around 7,000 to 12,000 rpm. It should be noted that using this technique may result in smaller sizes of atomized and cultivatable (stabilized) droplets. The size may be between roughly 10 μm to 50 μm. This technique may be used over the jetting and showering techniques in applications where higher dispersion of inoculated mixture is desired.

To illustrate the significance of adding surfactants to the inoculated mixture, a thin layer of aerosil may be placed at the bottom of a Petri dish. To a first Petri dish containing a thin layer of aerosil, droplets of Congo red dye (which has no surface activity) may be added to the aerosil layer. To a second Petri dish containing a thin layer of aerosil, droplets of 1% BSA solution may be added. To a third Petri dish containing a thin layer of aerosil, droplets of 2% agar solution may be added. To a fourth Petri dish containing a thin layer of aerosil, droplets of 0.1% Twen-80 solution may be added. The combination in each of the four Petri dishes may be gently stirred to allow aerosil to cover the droplets' entire surface. It should be noted that there may be droplets whose surface will not be completely covered. Stirring may be accomplished via, for example, a magnetic stirrer or a hand by rotating the Petri dish in a gyro-like/circular motion. Once full coverage is achieved, or is believed to have been achieved, each Petri dish may be tilted so that droplets can run to the lower side. This running may result in the droplets contacting the lower side of each Petri dish and/or forming one or more layers of droplets, which may be in contact with each other. In the case of droplets of pure water and/or water solutions lacking surface activity (e.g., dye solution), water droplets may coalesce within seconds after being brought into contact. BSA droplets in contact with each other may remain stable for about 15-30 mins. The agar droplets were also found to be stable. Stability is likely to be partly due to the agar's surface activity. Another reason for stability is that agar droplets tend to form spherical gel particles, which normally would not coalesce upon contact because of its solid nature. Droplets of 0.1% Twen-80 in contact with each other may remain stable for about 3-5 mins. Although stability may be achieved in certain scenarios, stability tends to be short-lived. Hence, certain surfactants may be added to inoculated mixture to keep suspended cultivatable droplets stable when introduced to a hydrophobic particle. Nonlimiting examples of such surfactants include laundry detergents, proteins (e.g., serum albumin, gelatin, casein, etc.), synthetic polymers (e.g., polyvinyl alcohol, poly-(vinyl-pyrrolidone), etc.), fatty acids, lipids, lipoproteins, glycolipids, etc. Complex biological mixtures (e.g., milk, blood, plasma, other biological fluids, plant extracts, etc.) may also be used to stabilize the cultivatable droplets suspended in aerosil and/or in a web of hydrophobic fibers.

Once stabilized, cultivatable droplets may be separated from remaining/excess aerosil particles. Because the density of aerosil particles tends to be substantially different from that of water, separation may be accomplished in a variety of ways. Examples include, but are not limited to, centrifugation, wind chamber, etc. The invention may subject cultivatable droplets to centrifugation, or an equivalent vortexing process (such as vortexing by hand/thumb). This aspect may be accomplished by placing cultivatable droplets in a centrifuge tube and spinning the tube in a centrifuge. The rate of spinning may vary in speed and length of time as determined by the user. For instance, cultivatable droplets may be centrifuged at about 2,000 revolutions per minute for about 5 minutes. However, it should be noted that there is no definitive rate or time that is necessary for separation so long as separation is achieved. When cultivatable droplets have collected at the bottom of a centrifuge tube, cultivatable droplets may be collected using a retrieving device, such as a pipette.

If wind chamber is exercised, air may be used to blow light aerosil particles away while cultivatable droplets fall and collect at the bottom of the wind chamber. If a user decides to exercise this method, aerosil may be collected and reused after sterilization.

However, it is not always necessary to separate the hydrophobic particles, or even excess hydrophobic particles, from cultivatable droplets. For instance, because silicon dioxide is frequently used in soil treatment, there is no need to remove the silicon dioxide from cell cultures that are grown for purposes of soil treatment, where silicon dioxide is used as the hydrophobic particle. Furthermore, since hydrophobic particles may limit the potential for the spread of contamination, it may be desirable to maintain cultivated cells within individual cultivatable droplets for storage purposes.

In most cases, the space between cultivatable droplets provides adequate aeration for the cell culture. It is a particularly useful and beneficial feature of the invention that the space existing between individual cultivatable droplets provides an optimum environment for the concentrated growth of cell cultures. Having adequate aeration helps allow the growing cultures to make optimal use of the mixture contained in each droplet.

However, one skilled in the art can readily see that various means may be exercised to provide the growing cell culture with supplemental oxygen (exogenous) and/or other exogenous gases to optimize aeration conditions. For example, a fermentation vessel or zone may be provided with a port opening on the vessel or zone through which exogenous molecular oxygen may be pumped via conduits to transport gas. Additionally, the fermentation vessel or zone may be further equipped with a second port opening for removal of gases during the fermentation process. By enhancing aeration, cell cultures may have more ease in dividing and consuming available mixture in a cultivatable droplet.

Optionally, culturing may also be facilitated by incubating the cells. Incubation may be regulated using various controllers, such as a temperature controller, atmospheric controller and a pressure controller. The temperature controller may be used to regulate the temperature. The atmospheric controller may be used to regulate atmospheric conditions. The pressure controller may be used to regulate pressure.

The cultivatable droplets may be placed in an environment where the cells may later interact. As more of the mixture is consumed, hydrophobic particles may disassociate from the cell cultures. This dissociation may allow the cells to come into contact and/or interact with the surrounding environment.

Figure 9:
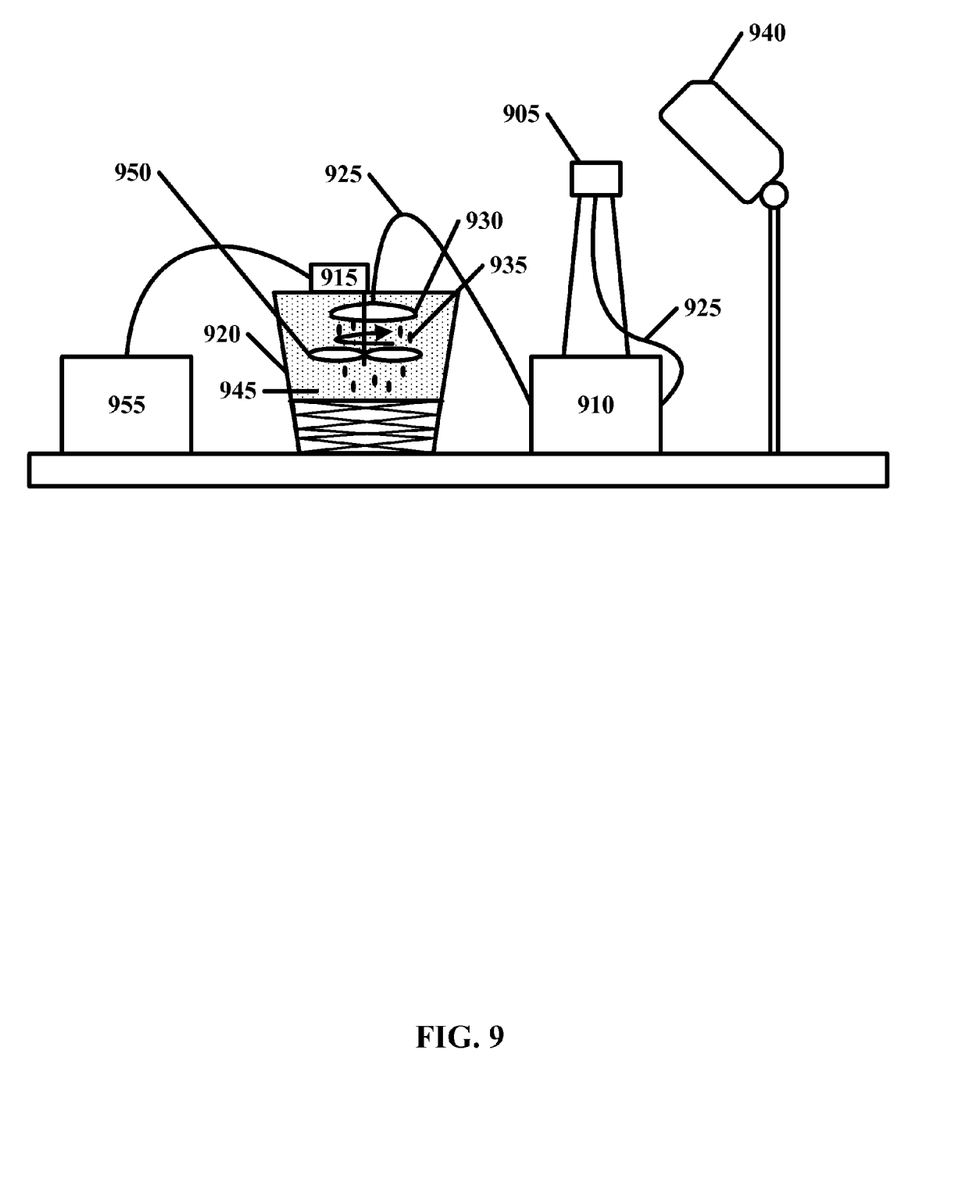
FIG. 9 shows a system for culturing cells, as per one embodiment of the invention.

Referring to FIG. 9, as an embodiment, the invention may overall involve a system encompassing an inoculator 905, a pump 910 and a vessel 920. The inoculator 905 may be used for creating an inoculated mixture comprising a cultivation medium, surfactant and plurality of cells. The inoculated mixture may be converted into cultivatable droplets 935 using a variety of techniques. Such techniques include, but are not limited to, the showering technique, the jetting technique, the blending technique, etc.

Using the showering technique as an example, the inoculated mixture can be converted into cultivatable droplets 935 by forcing the inoculated mixture through a shower-like head 930. A vessel 920 (e.g., Petri dish, bucket, bottle, jar, can, etc.) may be used to catch the cultivatable droplets 935. Nozzles 925 may be used to help transfer the inoculated mixture from the pump 910 to the vessel 920. The pump 910 may be, or function as, an electrostatic spraying device, humidifier or a dispenser.

The vessel 920 may be filled with a porous medium 945. The porous medium may contain hydrophobic particles. As cultivatable droplets 935 come into contact with the hydrophobic particles, the hydrophobic particles may adhere around each cultivatable droplet 935. The porous medium may be a hydrophobic powder, fibrous powder, etc. Particle adhesion may appear as a bead-like barrier around each cultivatable droplet. To aid in the coating and mixing (or stirring) process, a propeller 950 attached to a motor 915 may be used. To adjust rotational speed of the propeller 950, a speed controller 955 may be used. Once the desired amount of cultivatable droplets 935 is achieved, the cultivatable droplets 935 may be separated, albeit not necessary, from excess hydrophobic particles 945. The cultivatable droplets may be cultured in the vessel 920 or a substituted container.

At any point of the cell culturing process, an atmospheric controller may be used to regulate the atmospheric conditions. Similarly, a temperature controller may be used to control temperature settings; a pressure controller may be used to control pressure. It is also within the scope of the invention to use a lamp 940 as a source of heat. Moreover, to help optimize aeration conditions, a gas aerator may be used to provide the cultivatable droplets with supplemental exogenous gas, such as molecular oxygen.

It should be noted that alternative cultivatable droplet creation techniques, such as jetting and blending, can be exercised in lieu of, or in conjunction with, the showering technique. For example, where the pump sprays inoculated mixture into a vessel via showering, the vessel may also house a propeller having an array of holes smaller than the array of holes in the sprayer. Any cultivatable droplets passing through this propeller may be further decreased in size.

Experiments

I. Micorrhizal Fungus

Yeast mold (YM) media may be prepared using ATCC Protocol No. 36554. The media was inoculated with the Micorrhizal fungus by adding this fungus to the cultivation media until a final concentration of $10^6$ cells per ml as described in the protocol was achieved. Three Petri dishes having a diameter of 15 cm were filled with Aerosil® R 974, produced by DeGussa Corp. of Germany. Using the jetting method technique described herein, 15 ml of inoculated mixture was dispersed into the aerosil layer as cultivatable droplets having a diameter of about 1-2 mm. Three tubes, each containing 15 ml of cultivatable droplets, were used as controls. All tubes and dishes may be placed into a cabinet with a temperature at 24° C. and a humidity of 100%. The cells of the fungus in the tubes and in cultivatable droplets were grown for 3 days. After 3 days, the grown biomass was collected and centrifuged at 6,000 rpm for 10 minutes.

After collection, the sediments were analyzed under a phase-contrast microscope. Analysis indicated that only cells lacking hyphaes were observed in the control tubes. In contrast, cells grown in dispersed cultivatable droplets showed numerous hyphaes directed inside and outside the cultivatable droplets. Almost all space was filled with hyphae. This example illustrates an advantage of dispersed cultivatable droplets in inoculated mixture: providing a larger interfacial area for growth and differentiation of cells.

II. *Arthrobacter histidinolovorans*

Nutrient broth (NB) media may be prepared using ATCC Protocol No. 11442. The NB media was seeded with *Arthrobacter histidinolovorans* by adding this bacteria to the NB media until a final concentration of $10^6$ cells per ml as described in the protocol was achieved. Cultivatable droplets were prepared using the blending method technique described herein to disperse seeded media with Aerosil® R 974 in a 1:3 volume to volume ratio. Cultivatable droplets were distributed among six 45 ml tubes, where each tube contained 15 ml of cultivatable droplets. The contents of each tube were transferred to a Petri dish having a diameter of 10 cm. Control dishes were prepared with the continuous media (NB agar). Both Petri dishes with the dispersed media and control dishes with NB agar were placed in a humid chamber with a controlled temperature. The *Arthrobacter histidinolovorans* was grown for 48 hours at 20° C. After 48 hours, the *Arthrobacter histidinolovorans* cells were harvested from the Aerosil by centrifugation at 6,000 rpm for 10 minutes.

After collection, the colonies in the sediments and on the control agars were analyzed under a phase-contrast microscope. Analysis indicated that *Arthrobacter histidinolovorans* colonies readily grew in the cultivatable droplets suspended in Aerosil. The total number of colonies related to the unit volume of the media was approximately twice as many in control agars as compared to that in cultivatable droplets.

The foregoing descriptions of the embodiments of the invention have been presented for purposes of illustration and description. They are not intended to be exhaustive or be limiting to the precise forms disclosed, and obviously many modifications and variations are possible in light of the above teaching. The illustrated embodiments were chosen and described in order to best explain the principles of the invention and its practical application to thereby enable others skilled in the art to best utilize it in various embodiments and with various modifications as are suited to the particular use contemplated without departing from the spirit and scope of the invention. In fact, after reading the above description, it will be apparent to one skilled in the relevant art(s) how to implement the invention in alternative embodiments. Thus, the invention should not be limited by any of the above described example embodiments. For example, it is within the scope of this invention that cell-free biochemical and biosynthetic systems may be introduced into cultivatable droplets, which may be stabilized with hydrophobic microparticles or nanoparticles. In addition, the invention may be practiced over areas nears airports, where the cultured cells may consume airport runoff, deicing compounds or pollutant emissions from construction, maintenance or equipment. Furthermore, the invention may also be practiced as a detoxification unit over areas involving environmental cleanups (such as toxic chemical and/or biological spills), hospitals, waste-to-energy facilities, sewage treatment facilities, areas involving radioactive materials, etc.

In addition, it should be understood that any figures, graphs, tables, examples, etc., which highlight the functionality and advantages of the invention, are presented for example purposes only. The architecture of the disclosed is sufficiently flexible and configurable, such that it may be utilized in ways other than that shown. For example, the steps listed in any flowchart may be reordered or only optionally used in some embodiments.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical invention of the application. The Abstract is not intended to be limiting as to the scope of the invention in any way.

Furthermore, it is the applicants' intent that only claims that include the express language "means for" or "step for" be interpreted under 35 U.S.C. §112, paragraph 6. Claims that do not expressly include the phrase "means for" or "step for" are not to be interpreted under 35 U.S.C. §112, paragraph 6.

A portion of the invention of this patent document contains material which is subject to copyright protection. The copyright owner has no objection to the facsimile reproduction by anyone of the patent document or the patent invention, as it appears in the Patent and Trademark Office patent file or records, but otherwise reserves all copyright rights whatsoever.

What is claimed is:

1. A method for cultivating droplets of Micorrhizal fungus comprising:
   a. introducing at least one surfactant to a cultivation medium for creating a mixture;
   b. adding a plurality of cells comprising Micorrhizal fungus to the mixture;
   c. creating cultivatable droplets from the mixture having the cells; and
   d. stabilizing the cultivatable droplets by introducing the cultivatable droplets to a porous medium.

2. The method according to claim 1, further including aerating the cultivatable droplets with exogenous gas.

3. The method according to claim 1, further including culturing the cells within each of the cultivatable droplets.

4. The method according to claim 1, wherein a jetting technique is used to create the cultivatable droplets.

5. The method according to claim 4, wherein said jetting technique comprises providing a container including said porous medium to catch said cultivatable droplets.

6. The method according to claim 1, wherein the porous medium is a hydrophobic powder.

7. The method according to claim 1, wherein the porous medium is a fibrous powder.

8. The method for cultivating droplets of *Arthrobacter histidinolovorans* comprising:

a. introducing at least one surfactant to a cultivation medium for creating a mixture;

b. adding a plurality of cells comprising *Arthrobacter histidinolovorans* to the mixture;

c. creating cultivatable droplets from the mixture having the cells; and d. stabilizing the cultivatable droplets by introducing the cultivatable droplets to a porous medium.

9. The method according to claim 8, further including aerating the cultivatable droplets with exogenous gas.

10. The method according to claim 8, further including culturing the cells within each of the cultivatable droplets.

11. The method according to claim 8, wherein a blending method technique is used to create the cultivatable droplets.

12. The method according to claim 11, comprising using knives revolving between approximately 7,000 rpm and 12,000 rpm.

13. The method according to claim 12, wherein the size of said stabilized cultivatable droplets is between approximately 10 microns and 50 microns.

14. The method according to claim 8, wherein the porous medium is a hydrophobic powder.

15. The method according to claim 8, wherein the porous medium is a fibrous powder.

16. The method according to claim 1, wherein said porous medium comprises silanized particles.

* * * * *